(12) United States Patent
McKinnis et al.

(10) Patent No.: US 9,629,721 B2
(45) Date of Patent: Apr. 25, 2017

(54) PERIPHERAL SEALING VENOUS CHECK-VALVE

(71) Applicant: Muffin Incorporated, West Lafayette, IN (US)

(72) Inventors: Peter S. McKinnis, West Lafayette, IN (US); Neal E. Fearnot, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 0 days.

(21) Appl. No.: 14/175,092

(22) Filed: Feb. 7, 2014

(65) Prior Publication Data

US 2014/0228940 A1 Aug. 14, 2014

Related U.S. Application Data

(60) Provisional application No. 61/762,438, filed on Feb. 8, 2013.

(51) Int. Cl.
*A61F 2/24* (2006.01)
*A61F 2/01* (2006.01)

(52) U.S. Cl.
CPC ............ *A61F 2/2475* (2013.01); *A61F 2/01* (2013.01); *A61F 2/2415* (2013.01); *A61F 2/2436* (2013.01); *A61F 2002/016* (2013.01); *A61F 2220/0016* (2013.01); *A61F 2250/0037* (2013.01)

(58) Field of Classification Search
CPC ........ A61F 2/2475; A61F 2/2436; A61F 2/24; A61F 2/2415; A61F 2/2439
USPC .............................. 623/1.24, 1.26, 2.14, 2.18
See application file for complete search history.

(56) References Cited

U.S. PATENT DOCUMENTS

| 4,494,531 | A | * | 1/1985 | Gianturco | ...................... 606/200 |
| 5,324,304 | A | * | 6/1994 | Rasmussen | ................... 606/200 |
| 5,413,599 | A | * | 5/1995 | Imachi et al. | ............... 623/1.24 |
| 6,217,600 | B1 | * | 4/2001 | DiMatteo | ...................... 606/202 |
| 6,287,334 | B1 | * | 9/2001 | Moll et al. | ................... 623/1.24 |
| 6,319,281 | B1 | | 11/2001 | Patel | |

(Continued)

FOREIGN PATENT DOCUMENTS

WO    WO 2006/034233 A1    3/2006

OTHER PUBLICATIONS

International Search Report and Written Opinion issued in PCT/US2014/015203, dated Nov. 12, 2014, 15 pgs.

*Primary Examiner* — Alvin Stewart
(74) *Attorney, Agent, or Firm* — Woodard, Emhardt, Moriarty, McNett & Henry LLP

(57) ABSTRACT

Among other things, there are disclosed embodiments of a valve implant that in particular examples are implantable within a blood vessel, which include a first set of elongate members, a second set of elongate members, and a hood affixed to the first set of elongate members. The first set of elongate members is resiliently deformable, and their distal ends are flared radially outward. The distal ends of the second set of elongate members are distal to the ends of the first set of elongate members. The hood is affixed to the first set of elongate members, and seals against the interior wall of the blood vessel in an expanded configuration. When blood flows from the proximal to the distal side of the valve implant, it presses on the hood, compressing the first set of elongate members, breaking the seal.

21 Claims, 3 Drawing Sheets

(56) References Cited

U.S. PATENT DOCUMENTS

| | | | |
|---|---|---|---|
| 6,425,916 B1* | 7/2002 | Garrison et al. | 623/2.11 |
| 6,527,800 B1 | 3/2003 | McGuckin et al. | |
| 7,070,616 B2* | 7/2006 | Majercak et al. | 623/1.24 |
| 7,887,583 B2* | 2/2011 | Macoviak | 623/2.38 |
| 7,947,074 B2* | 5/2011 | Meretei | 623/2.14 |
| 8,070,802 B2* | 12/2011 | Lamphere et al. | 623/2.14 |
| 8,092,520 B2* | 1/2012 | Quadri | 623/1.36 |
| 8,133,251 B2* | 3/2012 | Ravenscroft et al. | 606/200 |
| 8,211,165 B1* | 7/2012 | McIntosh et al. | 623/1.24 |
| 8,246,675 B2* | 8/2012 | Zegdi | 623/1.24 |
| 8,257,434 B2* | 9/2012 | Matheny | 623/2.19 |
| 8,348,988 B2* | 1/2013 | Lad et al. | 623/1.13 |
| 8,398,672 B2* | 3/2013 | Kleshinski et al. | 606/200 |
| 8,545,553 B2* | 10/2013 | Zipory et al. | 623/2.37 |
| 8,562,638 B2* | 10/2013 | Sokolov et al. | 606/200 |
| 8,574,261 B2* | 11/2013 | Carr et al. | 606/200 |
| 8,613,754 B2* | 12/2013 | Chanduszko et al. | 606/200 |
| 8,685,086 B2* | 4/2014 | Navia et al. | 623/2.18 |
| 8,690,939 B2* | 4/2014 | Miller et al. | 623/2.11 |
| 8,795,318 B2* | 8/2014 | Hallisey et al. | 606/200 |
| 2001/0039450 A1* | 11/2001 | Pavcnik et al. | 623/1.24 |
| 2002/0123802 A1* | 9/2002 | Snyders | 623/2.18 |
| 2002/0193828 A1* | 12/2002 | Griffin et al. | 606/200 |
| 2003/0208224 A1* | 11/2003 | Broome | 606/200 |
| 2004/0019374 A1* | 1/2004 | Hojeibane et al. | 623/1.13 |
| 2004/0186558 A1* | 9/2004 | Pavcnik et al. | 623/1.24 |
| 2004/0225352 A1* | 11/2004 | Osborne et al. | 623/1.24 |
| 2004/0260389 A1* | 12/2004 | Case et al. | 623/1.24 |
| 2005/0096735 A1* | 5/2005 | Hojeibane et al. | 623/1.24 |
| 2006/0089708 A1* | 4/2006 | Osse et al. | 623/1.24 |
| 2006/0212110 A1* | 9/2006 | Osborne et al. | 623/1.24 |
| 2006/0265053 A1* | 11/2006 | Hunt | 623/1.24 |
| 2007/0027535 A1* | 2/2007 | Purdy et al. | 623/2.18 |
| 2007/0038295 A1* | 2/2007 | Case et al. | 623/2.18 |
| 2007/0043431 A1* | 2/2007 | Melsheimer | 623/1.24 |
| 2007/0093887 A1* | 4/2007 | Case et al. | 623/1.24 |
| 2010/0262232 A1* | 10/2010 | Annest | 623/2.17 |
| 2013/0006294 A1* | 1/2013 | Kashkarov et al. | 606/200 |
| 2013/0018453 A1 | 1/2013 | Case et al. | |

* cited by examiner

PERIPHERAL SEALING VENOUS CHECK-VALVE

The present disclosure relates to medical devices. More particularly, the disclosure relates to venous check valves, for emplacement within a blood vessel to permit blood flow in one direction, while effectively limiting or blocking flow in the other direction.

BACKGROUND

A number of bodily passages include valves for ensuring that material in the passage moves in generally one direction. For example, in all vertebrates blood is transported away from the heart and throughout the body via arteries and returns to the heart through veins. To allow for optimal transport of the blood, the arteries and veins include valves that keep the blood flowing in generally one direction through them. In the case of veins, to keep blood moving back toward the heart and to reduce blood pressure build-up, the vessels contain various valves within their lumens, which open to permit blood flow toward the heart and close to limit or prevent backflow of blood, i.e. return of blood toward the extremities. In the case of an artery, valves open to permit blood flow away from the heart and close to limit or prevent backflow toward the heart.

Problems can arise when these valves fail to function properly. For instance, venous valves can become incompetent or damaged (e.g. by disease) such that the backflow of blood is not prevented. When this occurs, blood pressure builds up and the veins and their valves become dilated, particularly in the lower extremities. If enough pressure builds, the condition of venous insufficiency may develop. The severity of this condition is substantial, resulting in swelling, extensive pain, deformities and, in the most severe cases, the development of ulcers can occur. If these ulcers become infected, amputation may ultimately be necessary.

Initial treatments for venous insufficiency have included elevation of the legs or the use of compression stockings. If surgery is determined to be necessary, vein stripping is often performed, which involves the removal of the incompetent or damaged vein(s).

The development of artificial and biological valves has also been suggested to return normal pressure to the veins. There are a variety of these valves described in the art, which are generally designed to allow normal flow of blood back to the heart, while restricting retrograde flow. However, there remains a needs for improved and/or alternative valve devices and methods, such as for modifying blood flow within vessels on at least a temporary basis. In particular, use of known devices poses risks of thrombogenesis, which must be weighed against the therapeutic effects. Devices that reduce the likelihood of thrombogenic stenosis would provide potential treatments for a wider range of patients and indications. The present disclosure is addressed to these needs.

SUMMARY

Among other things, there are disclosed embodiments of valve implants, in particular examples designed for implantation within the lumen of a blood vessel, in certain embodiments comprises a first set of elongate members, a second set of elongate members, and a hood affixed to the first set of elongate members. The elongate members of the first and second sets each have a proximal end adjacent to one another, and a distal end. The first set of elongate members is resiliently deformable, and their distal ends are flared radially outward. The distal ends of the second set of elongate members are distal with respect to the ends of the first set of elongate members. In the vascular valve implant's relaxed state, the hood affixed to the first set of elongate members engages and/or seals against the interior wall of the blood vessel. When blood attempts to flow from the proximal to the distal side of the valve implant, it presses on the hood, compressing the first set of elongate members, thereby disengaging the members from the vessel wall, releasing the seal and allowing flow.

Thus, particular examples of valve implants for implantation in a bodily lumen have a central axis, a proximal end, and a distal end. A first set of resiliently deformable, elongate members each have respective proximal and distal ends, the proximal ends adjacent to one another, and respective distal ends are flared radially outward. A second set of elongate members each have respective proximal and distal ends, with those proximal ends adjacent to the proximal ends of the first set of elongate members, and the distal ends both flared radially outward and distal to the distal ends of the first set of elongate members. A substantially fluid-tight hood is affixed to the first set of elongate members, the hood and first set of elongate members forming a concavity. At least part of the hood is collapsible toward the central axis when blood flows in a direction generally from the proximal end to the distal end, thereby allowing blood to flow past the vascular implant.

Other embodiments include a collar that affixes the proximal ends of the elongate members to one another. The elongate members may be made from a biocompatible material, such as nitinol, and/or from an echogenic material (e.g. one enabling visualization via ultrasound). In particular examples, a torsion spring is affixed to the distal ends of one or more of the second set of elongate members, or such end(s) may form torsion springs. The elongate members of either or both sets may be formed as wires. The hood may be formed of or include extracellular matrix and/or endothelial colony forming cells, such as a basement membrane with the endothelial colony forming cells being implanted on the basement membrane. Specific implants are sized and configured for placement in a blood vessel, as for example a peripheral vein in which an existing valve has been damaged or its function has deteriorated.

In some embodiments, a valve implant for placement within a patient includes a set of resiliently deformable struts, the struts each having respective proximal and distal ends and a middle portion, with the middle portions and distal ends of the struts flaring outward with respect to each other so that the struts together have a generally bulbous aspect. The struts have a first open configuration toward which the struts are biased and are resiliently bendable to a second configuration in which the distal ends of one or more of the struts are closer to each other than they are in the open configuration. A substantially fluid-tight hood is affixed to a plurality of the struts, the hood forming a concavity having a mouth with a first width when the struts are in the open configuration and a second smaller width when the struts are in the second configuration, and the hood having an exterior surface opposite the concavity. A set of elongated legs each having respective proximal and distal ends can also be included, with the distal ends of the elongated legs being flared radially outward and being further from the proximal ends of the struts than the distal ends of the struts are from the proximal ends of the struts.

In examples of implants for implantation in a blood vessel, the struts may have a spring constant such that when flow in the blood vessel normal for the patient presses on the exterior surface of the hood when the struts are in the open configuration, the struts and hood compress toward the second configuration and allows flow past the hood. The distal end of at least one leg can include a foot that engages the inside of the vessel, and such a foot may be or otherwise include a torsion spring. In some embodiments, the hood comprises an easily and/or rapidly endothelializable material, such as a collagenous material. Examples in which the proximal ends of the struts are adjacent and fixed to each other, and/or in which the proximal ends of the legs are adjacent and fixed to each other, are also disclosed.

Methods for making and using the embodiments noted above are also disclosed. As will be understood from the description herein, valve implants according to this disclosure have significant advantages over currently available valve prostheses and other methods of addressing valve failure.

DESCRIPTION OF THE ILLUSTRATED EMBODIMENTS

Figure 1:
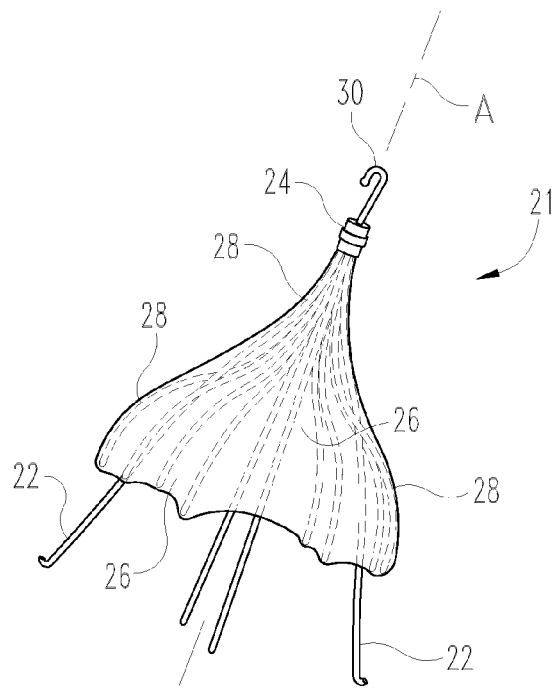
FIG. 1 is a perspective view of a peripheral sealing check valve according to one embodiment of the present disclosure.

For the purposes of promoting an understanding of the principles of the disclosure, reference will now be made to the embodiment illustrated in the drawings, and specific language will be used to describe the same. It will nevertheless be understood that no limitation of the scope of the claims is thereby intended, and alterations and modifications in the illustrated device, and further applications of the principles of the disclosure as illustrated therein, are herein contemplated as would normally occur to one skilled in the art to which the disclosure relates.

Valve implants as described herein provide treatments for vascular insufficiency, and other such conditions. Such implants are flexible and deformable, and are suitable for use in peripheral blood vessels, or other locations which are frequently deformed or at least partially collapsed, due to natural stresses such as external pressure or muscle flexing. The implant can be easily emplaced by familiar and proven, minimally invasive methods, such as by intravenous catheter. Although the vascular implants can be permanent, if the need arises they can also be removed by such methods. Valve implants according to the present disclosure provide a valuable improvement over existing vascular valve implants, because they provide an alternative valve structure, and can reduce the likelihood that the vein will become blocked due to thrombogenic stenosis.

Referring now generally to the drawings, there is shown an exemplary type of peripheral sealing venous valve implant 20 for use in the circulatory system, to permit blood flow within a blood vessel in one direction, while effectively inhibiting or preventing it in the other direction. Implant 20 generally features a skeleton or frame 21 on which a hood or covering 51 is attached. As will be discussed further below, in certain embodiments valve implant 20 is inserted into and at least temporarily emplaced or fixed within a vessel (e.g. vein or artery), inhibiting blood flow in a first direction, indicated in FIG. 4 (see arrows F), namely, in the direction from the distal side of the implant 20 to the proximal side of implant 20.

Figure 2:
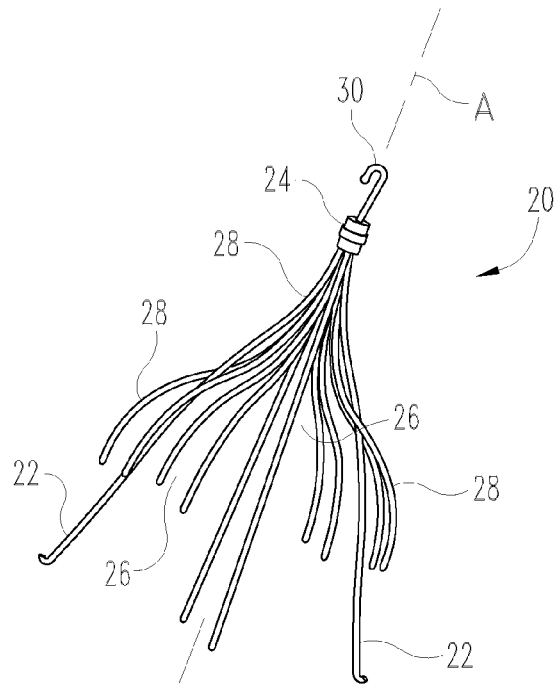
FIG. 2 is a perspective view of a frame or skeleton for a peripheral sealing check valve according to the present disclosure.

As shown in FIG. 2 (with the hood 51 uninstalled), frame or skeleton 21 in that illustrated embodiment includes a series of elongate members 22 and 28, which are joined by a collar or crimp 24 near or at their respective proximal ends and are separated distal of those proximal ends by gaps 26. Skeleton 21 is depicted with eight shorter wires or struts 22 and four longer wires or legs 28, whose separate functions are described in greater detail hereinbelow, but it will be appreciated that the precise number of wires is not critical to the operation of valve implant 20.

In an unstressed (e.g. non-compressed) condition, wires 22 and 28 form a somewhat outwardly-flared device, with the free ends of wires 22 and 28 positioned radially outward and longitudinally displaced from collar 24. The illustrated embodiment shows wires or struts 22 having a curvature creating a generally bulbous overall form for wires 22, in the unstressed condition. Wires or legs 28 also flare outward, but include a somewhat straight middle portion, between collar 24 and a distal end or foot. Thus, the skeleton 21 has a larger downstream aspect or dimension at those free ends, and it narrows to collar 24.

Figure 3:
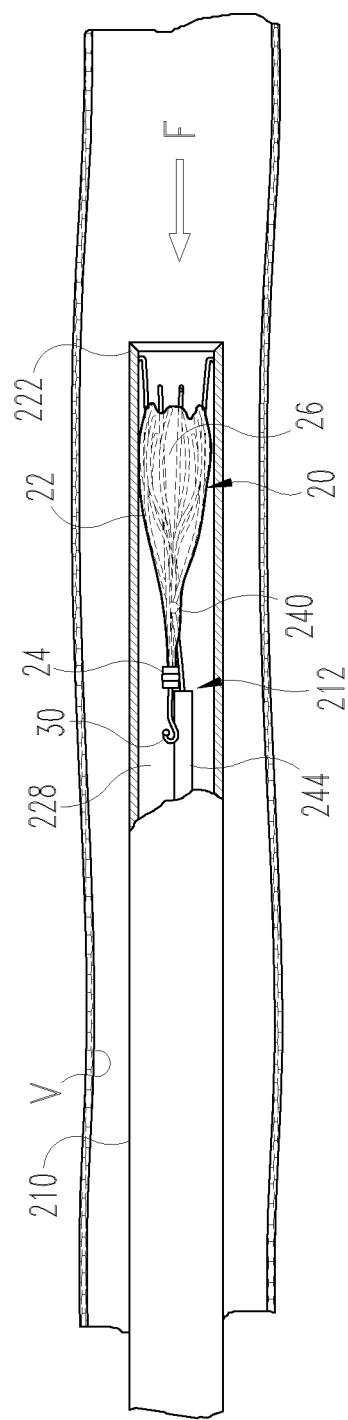
FIG. 3 is a part-cross-sectional view illustrating the delivery by catheter of a venous check valve according to the present disclosure.

Elongate members 22 and 28 are single strands of thin wire, in specific embodiments, made of biocompatible materials such as stainless steel, Nitinol or other superelastic material(s), combinations of such superelastic materials with other compatible materials, or other flexible and sturdy material. In any event, at least elongate members 22 are resiliently deformable, so that valve implant 20 is generally collapsible toward and expandable from a longitudinal axis A through collar 24. Wires 28 may also be resiliently flexible, especially in their middle portion. Thus, as shown in FIG. 3, wires 22 and 28 can be flexed in toward axis A for enclosure in a catheter or other transport device (e.g. 210 in FIG. 3) for placement in a vessel, and, for example, when installed through a catheter within the vessel, wires 22 and 28 expand to or toward a natural or unstressed condition. Similarly, wires 22 deform to allow the valve implant 20 to compress and allow blood flow from the proximal to distal side. The wires 22 have a spring constant chosen so that the pressure of distal blood flow (i.e., indicated by arrows in FIG. 5, or opposite to direction F in FIG. 4) presses on an exterior of hood 51, compressing it and wires 22, breaking the seal around the walls 42 of the blood vessel, allowing blood to pass. Conversely, when blood attempts to flow in direction F, or stops flowing opposite to direction F, the hood 51 substantially seals against the internal walls 42 of the lumen 44, preventing the blood from passing the valve implant 20. The physical dimension of the implant 20 varies according to the site of implantation, but is generally chosen so that the distal ends of wires 22 (i.e. ends furthest from collar 24) make firm but, preferably, minimally traumatic contact with internal tissue wall(s) when implant 20 is in an unstressed or natural condition (e.g. not under compression or expansion), and so that legs 28 press against or into tissue to hold implant 20 in place within the body.

Wires 22 and 28 are, in certain embodiments, made of a suitable echogenic material (that is, a material having significant attenuating affect on ultrasound energy). Examples include the previously mentioned stainless steel, Nitinol, and the like. Use of such echogenic materials facilitates positioning ultrasound, e.g. intravascular ultrasonic (IVUS) positioning. In other embodiments wires 22 and 28 can be made largely or entirely from sturdy biocompatible plastics or other such materials.

Figure 6:
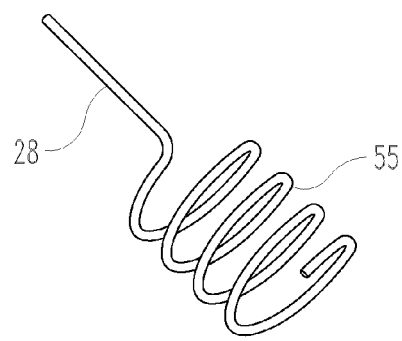
FIG. 6 is a perspective view of the distal end of one leg of certain embodiments of a valve implant according to the present disclosure, which forms a torsion spring.

In order to facilitate implantation in a peripheral vessel, as well as positioning via intravascular ultrasound, an illustrated embodiment of ends or feet 55 of wires 28 end in, or within, torsion springs 56 (e.g. FIG. 6). Torsion springs 56 have the advantage of providing a good footing for wires 28 to implant in or engage an interior vascular or other tissue wall, in order to secure valve implant 20 sufficiently securely in the desired position. They also are easily seen during ultrasound positioning, as their shape allows torsion springs to always present a surface portion perpendicular to the ultrasound waves or signals. One or more feet 55 of wires 28 may also or alternatively be provided with barbs or outwardly flared tips (e.g. on or in lieu of one or more torsion spring) to facilitate engagement with an internal vascular or other tissue wall.

Collar 24 generally forms a first, proximal end for relative upstream placement within a vessel, so that free, distal ends of wires 22 and 28 extend in a direction generally away from collar 24 to a relative downstream location. Collar 24 may be formed, for example, from the ends of elongate members 22 and/or 28, for example, by twisting them together, or may be a separate element that crimps or otherwise binds the elongate members 22 and/or 28 adjacent to one another, whether by adhesion, binding, or other suitable means. The exemplary valve implant 20 is also shown with a hook 30, which can be used to retrieve or position valve implant 20. Hook 30 may be fixed to or a part of collar 24, or may be an extension of one or more of wires 22 and/or 28.

Hood 51 is a generally or completely fluid impermeable, and as noted above is attached to at least a portion of the skeleton 21 so as to create a barrier to blood flow between the gaps 26 between individual wires 22 (not all of which are numbered in the drawings to maintain clarity). In the illustrated embodiment, hood 51 is shaped to fit wires 22 when skeleton 21 is in its relaxed or unstressed state without substantial tension, facilitating easy assembly, and be able to expand and contract with wires 22 (or have wires 22 expand or contract with it). Hood 51 forms an impermeable concavity, in the general bulbous or flared shape of wires 22, such as the shape of a pear, garlic clove, or the like. Hood 51 is fixed to struts 22 so that when struts 22 are in their relaxed or unstressed condition, at least a portion (e.g. an edge or adjacent portion) of hood 51 engages tissue (e.g. of a vessel) around all or substantially all of its inner circumference, and fluid pressure on the outside of hood 51 causes hood 51 and attached struts 22 to move inward or collapse toward longitudinal axis A, overcoming the bias of struts 22. Legs 28 are positioned on the interior of hood 51 in the illustrated embodiment, and in such cases the middle portion of one or more legs 28 may bend when hood 51 and one or more struts 28 move inward (see e.g. FIG. 5). It will be understood that in other embodiments legs 28 may be placed outside hood 51. Struts 22 and hood 51 should be shaped and positioned so as to avoid disturbing the sites of implantation of feet 55 of legs 28 in the wall of the blood vessel or other tissue, by either expansion or collapse of hood 51 and struts 22 under distal blood flow. This can be facilitated by increasing the length of legs 28 relative to struts 22, i.e., having the length of legs 28 measured from collar 24 be substantially greater than the length of struts 22 measured from collar 24.

Hood 51 is of a collagenous biological material or mixture in particular embodiments, so as to serve as a scaffold or host for rapid endothelialization. In particular embodiments, fibroblasts are cultured in a cell culture dish of the desired shape (e.g. the general pear or garlic shape of the concavity formed by hood 51 on skeleton 21 in its relaxed state), and allowed to lay down a collagenous extracellular matrix (ECM). A suitable size and configuration of cell culture dish can be provided in conjunction with the valve implant 20. Once the extracellular matrix has been grown, the fibroblasts are devitalized. Human derived vascular endothelial cells (HUVEC) are then implanted onto the ECM, and allowed to lay down a basement membrane ("paving"). The HUVEC cells are then devitalized. Residual endotoxin levels are reduced to suitable levels for implantation. At this stage, hood 51 can be attached to skeleton 21, for example by inserting the ends of wires 22 longitudinally through hood 51 at a series of points along their length, or by using a suitable adhesive to attach hood 51 within or around wires 22. Alternatively, skeleton 21 can be introduced into the cell culture dish initially, and some or all of hood 51 grown around or along skeleton 21, e.g. to enclose wires 22. This may be done either by introducing skeleton 21 during the initial phase, during growth of the ECM, or during a later point, with each preceding step repeated in order to grow another layer of suitable ECM on the opposite side of wires 22. In certain embodiments, the ECM encloses both wires 22 and the upstream portion of wires 28. Hood 51 can be lyophilized, if desired, and sterilized prior to implantation.

In order to further facilitate rapid endothelialization, the hood 51 can be seeded with endothelial colony forming cells (ECFC). In addition to the cell culture dish, a bioreactor can also be provided in conjunction with the valve implant 20. ECFCs can be introduced into the bioreactor with the valve implant 20, and provided sufficient time to attach to the hood 51 prior to implantation.

Figure 4:
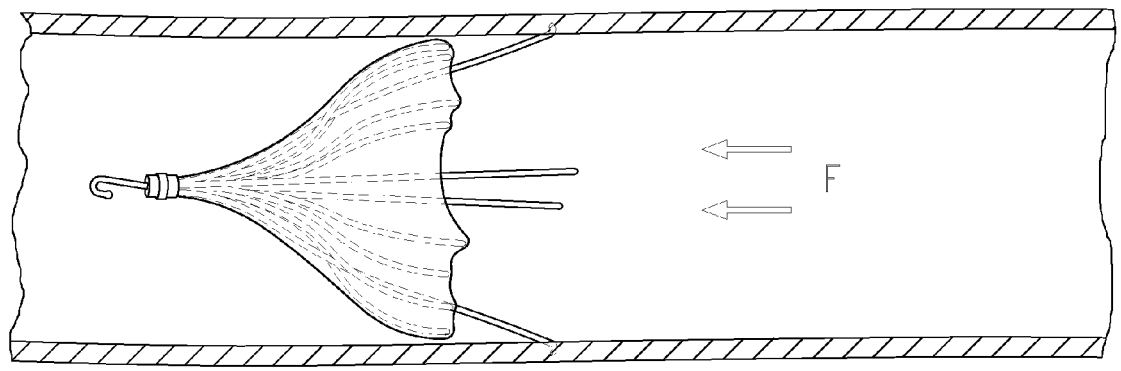
FIG. 4 is a part-cross-sectional view illustrating a venous check valve according to the present disclosure, emplaced within a peripheral blood vessel, while blocking retrograde flow.
Figure 5:
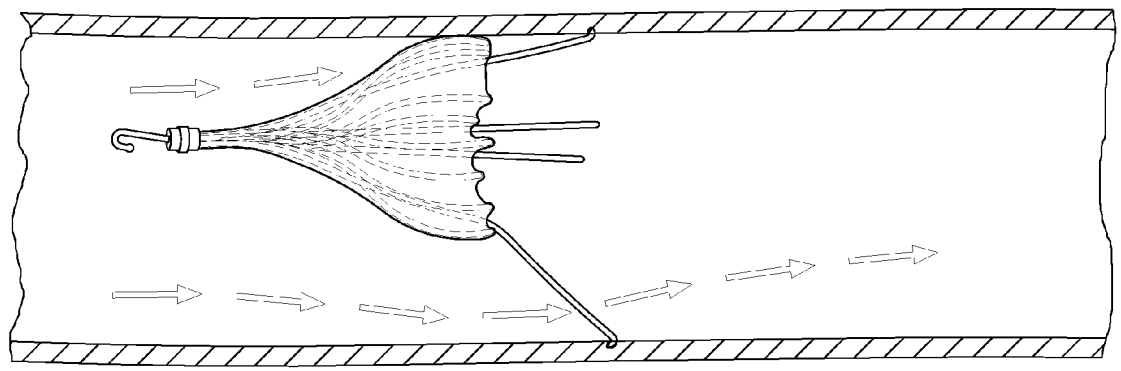
FIG. 5 is a part-cross-sectional view illustrative a venous check valve according to the present disclosure, emplaced within a peripheral blood vessel, while permitting antegrade flow to pass the valve.

FIGS. 4 and 5 show the valve implant 20 implanted in the lumen 44 of a blood vessel V, and description of such a placement is given below. While blood vessels (e.g. a vein) have been used as the principal example of a location for placement of embodiments of valve implant 20, it will be understood that embodiments of implant 20 can be used in other vessels, organs or body parts where it is desired to allow flow of fluid in generally a single direction.

Access to the vessel V is established. In particular embodiments, a cannula, sheath or other entry device (not shown) is placed through the skin of the patient to allow access into a major blood vessel (e.g. the femoral vein). A sheath, catheter or other conduit 210 is inserted into the patient via that access and maneuvered via the vasculature into vessel V so that a tip or end portion 212 is at a desired location in vessel V (e.g. at or adjacent a diseased, missing, non-functioning or otherwise faulty valve). In particular embodiments, a device 20 in a compressed form is placed within conduit 210, e.g. at or adjacent its tip or end portion 212, prior to insertion of conduit 210, while in other embodiments, a compressed device 20 might be moved through conduit 210 and into the body after conduit 210 is placed in vessel V. Conduit 210 may be adjusted longitudinally, laterally, and/or rotationally with respect to device 20 and/or vessel V as may be indicated or needed to place device 20 in the desired location and orientation relative to vessel V. As may be appreciated, additional steps during or prior to placement and maneuvering of the conduit may be performed, such as blocking some or all of the flow through vessel V. When the end portion of the conduit is in a desired location, device 20 is ejected into vessel V, as by pushing or pulling it out of conduit 210 (a pusher 214 is schematically indicated in FIG. 3). Once free of the conduit, struts 22 (with hood 51) and legs 28 expand to or toward a relaxed, unbiased or natural state, so that feet 55 (e.g. springs 56) engage or penetrate some of wall 42 within lumen 44 of vessel V, and so that struts 22 and hood 51 enlarge so that hood 51 contacts wall 42 to create the seal noted above. Observation of device 20 (as by x-ray or ultrasound imaging) may be performed to assure proper placement and engagement of device 20 within vessel V, and conduit 210 can then be removed.

Generally, when valve implant 20 is placed in vessel V its legs 28 hold valve implant 20 in place by engaging walls 42 of vessel V within lumen 44, and legs 28 do not disengage walls 42 while implant 20 operates. Wires or struts 22 with hood 51 in place perform the valve function of the implant 20. As will be appreciated, healthy endothelial cells inhibit thrombogenicity. Thus, in the illustrated embodiment, the enclosure of most of the skeleton 21, and the entire valve portion of the implant 20, within the hood 51 (which can rapidly endothelialize) reduces the chance of stenosis compared to existing valve implants. Legs 28 in the illustrated embodiment are long enough to separate the site of their engagement with wall 42 (and any potential resulting irritation) from hood 51, in order to foster rapid endothelialization of hood 51 and perhaps surrounding parts. Wire materials (in some embodiments) are spatially removed from hood 51, which limits or prevents blood flow, where a danger of stenosis may be concentrated.

In certain embodiments, valve implant 20 can be positioned with its central axis A generally positioned at or along the central axis of the lumen, held in place by the longer legs 28. Alternatively, valve implant 20 can be implanted generally against one side of the vessel, as more clearly shown in FIG. 5. In those embodiments in which the valve implant is positioned nearer to one side of the vessel, the wires 22 may either splay out farther toward the opposite side of vessel V, or, alternatively, the tension in the wires 22 may simply translate the valve implant 20 so that its central axis A moves towards the center of the vessel.

When blood in the vessel V attempts to flow in direction F, or the flow is insufficient to overcome the outward bias of struts 22 (as between heart beats or surges of blood in the desired direction), the hood 51 and struts 22 expand away from the central longitudinal axis A. Flow in direction F results in blood entering the concavity within hood 51, and the force from that flow with the bias of struts 22 results in portions (e.g. edges) of hood 51 engaging and sealing against walls 42 of vessel V around at least substantially the entire perimeter of lumen 44, effectively limiting or blocking further blood flow in direction F. Conversely, when blood flows opposite the direction F, e.g. during a systole or at other time when blood is forced in the desired direction, the blood presses on the outer surface of hood 51 (i.e. opposite to the concavity in hood 51). That force acts through hood 51 on wires 22, moving hood 51 and wires 22 inward against the bias of wires 22, resulting in at least a partial collapse of hood 51, breaking the seal between hood 51 and wall 42 of vessel V at one or more locations around lumen 44. Flow in the direction opposite direction F is thus allowed around valve implant 20. The peripheral seal and release with changes in direction and/or intensity of flow reduces the danger of thrombogenesis at the location of valve implant 20, by eliminating eddy patterns in the flow where static blood can coagulate.

It will be appreciated that, contrary to the way they are generally depicted in drawings, blood vessels in the body are frequently deformed, due to both internal or external pressures. For example, when an arm or leg is bent, the vessels in the body part that is bent or supporting pressure are also bent and/or may be squeezed (partially or completely closed) during such bending or normal use of the body part. Such bending or pressure is accommodated by natural vascular valves, which can be deformed during normal use of the body part and return to their former condition and operation. Valve implant 20 as disclosed herein is likewise sufficiently flexible and compressible to operate properly under these conditions.

While certain embodiments have been illustrated and described in detail in the drawings and foregoing description, the same is to be considered as illustrative and not restrictive in character. All changes and modifications that come within the spirit of the claims are desired to be protected. Features or attributes noted with respect to one or more specific embodiments may be used or incorporated into other embodiments of the structures and methods disclosed.

What is claimed is:

1. A valve implant for implantation in a bodily lumen, the implant having a central axis, a proximal end, and a distal end, the implant comprising:
   a first set of resiliently deformable, elongate members, each having respective proximal and distal ends, the proximal ends adjacent to one another, and respective distal ends flared radially outward, and wherein a plurality of the first set of resiliently deformable, elongate members each have a portion with a concave curvature that smoothly adjoins a portion with a convex curvature;
   a second set of elongate members, each having respective proximal and distal ends, the proximal ends adjacent to the proximal ends of the first set of elongate members, and the distal ends being free and both flared radially outward and distal to the distal ends of the first set of elongate members;
   a substantially fluid-tight hood affixed to the first set of elongate members, the hood and first set of elongate members forming a concavity;
   wherein at least part of the hood is collapsible toward the central axis when blood flows in a direction generally from the proximal end to the distal end, thereby allowing blood to flow past the vascular implant.

2. The valve implant of claim 1, further comprising a collar that affixes the proximal ends of at least one of the sets of the elongate members to one another.

3. The implant of claim 2, wherein the hood extends at least to the collar.

4. The valve implant of claim 1, wherein the elongate members are made from a biocompatible material.

5. The valve implant of claim 1, wherein at least one of the elongate members are made from an echogenic material.

6. The valve implant of claim 1, wherein torsion springs are affixed to the distal ends of the second set of elongate members.

7. The valve implant of claim 1, wherein the distal ends of the second set of elongate members form torsion springs.

8. The valve implant of claim 1, wherein at least one of the elongate members are wires.

9. The valve implant of claim 1, wherein the hood comprises extracellular matrix.

10. The valve implant of claim 1, wherein the hood comprises endothelial colony forming cells.

11. The valve implant of claim 10, further comprising a basement membrane, the endothelial colony forming cells being implanted on the basement membrane.

12. The valve implant of claim 1, wherein the valve implant is sized and configured for placement in a blood vessel.

13. The implant of claim 1, wherein the implant is for implantation in a blood vessel, and wherein the first set of resiliently deformable, elongate members have a spring constant such that when flow in the blood vessel normal for a patient presses on an exterior surface of the hood when the first set of resiliently deformable, elongate members are in an open configuration, the first set of resiliently deformable, elongate members and hood compress and allow flow past the hood.

14. The implant of claim 13, wherein the distal end of at least one of the second set of elongate members includes a foot that engages the inside of the vessel.

15. The implant of claim 14, wherein the foot includes a torsion spring.

16. The implant of claim 1, wherein the hood comprises an easily endothelializable material.

17. The implant of claim 16, wherein the material is a collagenous material.

18. The implant of claim 1, wherein the proximal ends of the first set of resiliently deformable, elongate members are adjacent and fixed to each other.

19. The implant of claim 1, wherein the proximal ends of the second set of elongate members are adjacent and fixed to each other.

20. The implant of claim 1, wherein the hood is external of at least part of the second set of elongate members.

21. The implant of claim 1, wherein a portion of a plurality of the second set of elongate members is within the hood.

* * * * *